United States Patent [19]

Tietjen et al.

[11] Patent Number: 4,578,266

[45] Date of Patent: Mar. 25, 1986

[54] SILICONE-BASED COSMETIC PRODUCTS CONTAINING PIGMENT

[75] Inventors: Marlene Tietjen, New York; Ivonne Brown, Roosevelt; Ralph A. Macchio, Middletown, all of N.Y.

[73] Assignee: Revlon, Inc., New York, N.Y.

[21] Appl. No.: 518,498

[22] Filed: Jul. 29, 1983

[51] Int. Cl.$^4$ ............................................. A61K 7/021
[52] U.S. Cl. .................................... 424/63; 424/64; 424/DIG. 5; 514/772
[58] Field of Search ................ 424/63, 64, 69, 70, 424/357, DIG. 5; 106/308 Q; 514/772

[56] References Cited

U.S. PATENT DOCUMENTS

| | | | |
|---|---|---|---|
| 2,101,843 | 12/1937 | Factor et al. | 424/63 |
| 3,649,321 | 3/1972 | Durrant et al. | 106/300 |
| 3,864,140 | 2/1975 | Ferrigno | 106/308 Q |
| 4,061,503 | 12/1977 | Berger et al. | 106/300 |
| 4,126,679 | 11/1978 | Davy et al. | 424/66 |
| 4,169,912 | 10/1979 | Schonafinger et al. | 428/145 |
| 4,342,742 | 8/1982 | Sebag et al. | 424/70 X |
| 4,344,799 | 8/1982 | Kohler et al. | 106/300 |
| 4,355,046 | 10/1982 | Siiess | 514/772 |
| 4,390,524 | 6/1983 | Nasuno et al. | 424/63 |
| 4,423,032 | 12/1983 | Abe et al. | 424/70 |

FOREIGN PATENT DOCUMENTS 1125659  6/1982  Canada ................ 424/63

OTHER PUBLICATIONS

Chem. Abs. 96:40742 (1982).
Chem. Abs. 95:12586v (1981).
Chem. Abs. 97:203104n (1982).

*Primary Examiner*—Sidney Marantz
*Assistant Examiner*—Shawn P. Foley

[57] ABSTRACT

Unexpectedly high amounts of pigment can be incorporated in anhydrous, pigmented cosmetic compositions containing an organically substituted polysiloxane by providing the pigment in a hydrophobic silicone coating.

14 Claims, No Drawings

SILICONE-BASED COSMETIC PRODUCTS CONTAINING PIGMENT

BACKGROUND OF THE INVENTION

This invention relates to pigmented cosmetic products in stick, cake, or cream form such as eyeshadows, foundations, moisturizers, and skin protecters. More specifically, the invention relates to such cosmetic products which contain a silicone base, e.g. dimethylpolysiloxane fluid. This fluid has the chemical formula

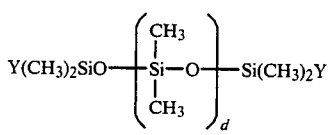
(1)

wherein both Y substituents are —CH$_3$, or both are —OH, and in which the degree of polymerization d is a value, typically between 1 and 150, effective to give the fluid a viscosity of 0.65 to 1 million centistokes at 25° C. (Viscosity of such fluids can be measured by widely recognized test methods, such as the spinning cup test.)

Although dimethylpolysiloxane and other silicone fluids offer the properties of water repellency, slip, non-greasy emollience, and low penetration of the skin, their use in anhydrous pigmented cream, cake and stick products is limited by the difficultly of dispersing inorganic pigments in the silicone base. The result is that such products contain only small amounts of pigment, or contain pigment which forms uneven color streaks in the final product.

It is therefore highly desirable to incorporate inorganic cosmetic pigments readily into a cosmetic product which contains a silicone fluid or a mixture of such fluids.

SUMMARY OF THE INVENTION

The invention comprises anhydrous, pigmented cosmetic products comprising a base of dimethylpolysiloxane having formula (1) above or mixtures of dimethylpolysiloxane with the organo-polysiloxanes having formula (2), (3) or (4) given below, or mixtures thereof, in which the pigment is easily dispersed and remains uniformly distributed without separating or segregating even at the unusually high pigment contents of 40 to 60 wt. %.

The more dispersible pigment comprises hydrophobic, finely divided particles of inorganic pigment whose surface is chemically bonded to, and physically completely coated by, polysiloxane.

By "more dispersible" we mean that by comparison to the same pigment in uncoated form, the coated pigment is dispersed uniformly throughout the cosmetic composition more easily and quickly during formulation of the composition, and it stays dispersed instead of settling or segregating out of the composition.

DETAILED DESCRIPTION OF THE INVENTION

Cosmetic compositions in accordance with this invention can contain a total of 10 to 70 wt. % of silicone compounds having formula (1). Alternatively, the compositions contain 10 to 70 wt. % of a combination of compound (1) and one or more compounds having formulas (2), (3) or (4), provided that at least 10 wt. % of the composition is dimethylpolysiloxane of formula (1). The other silicone compounds, any one, two, or three of which are included with the dimethylpolysiloxane, can be included in any amount provided that the total of silicones (1)-(4) is up to about 70 wt. % and provided that the combination of those compounds is a stable, homogeneous one-phase mixture at room temperature (25° C.). The preferred range of the total amount of compounds of formulas (1)-(4) is 20-50 wt. %, in which case dimethylpolysiloxane comprises at least 20 wt. % of the composition.

Formula (2) is an organosilane:

wherein R is alkyl having 1 to 30 carbon atoms, or aryl.

Formula (3) is an organo-polysiloxane:

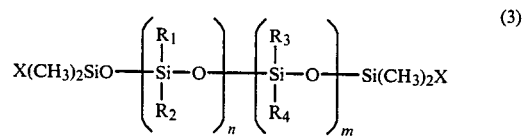

wherein $R_1$ and $R_3$ are independently alkyl having 1 to 30 carbon atoms or aryl; X is alkyl or alkyl-oxy and has 1 to 30 carbon atoms; $R_2$ is alkyl having 2 to 30 carbon atoms, aryl, or trimethylsiloxy $(CH_3)_3SiO-$); $R_4$ is alkyl having 1 to 30 carbon atoms, or aryl; n is 1 to 100; m is b 0 to 100; and (n plus m) is 1 to 100.

Formula (4) is cyclomethicone:

As used herein, "alkyl" and the alkyl moities of alkyl-oxy includes straight- and branched-chain aliphatic groups containing 1 to 30 carbon atoms; examples include methyl, ethyl, octyl, and octadecyl. Preferred aryl groups include phenyl and groups in which a phenyl ring is connected to the Si by an alkyl or alkylene bridge up to 3 carbon atoms long, such as styryl.

Preferred dimethylpolysiloxanes of formula (1) have a viscosity of about 5 to about 500 centistokes (abbreviated herein as "cs").

Examples of organo-polysiloxanes of formula (3) where m equals zero are polymethyloctyl-siloxane, polymethyloctadecyl-siloxane, polyphenyltrimethylsiloxy-siloxane, polymethylphenyl-siloxane, and octadecyloxydimethylpolydimethyl-siloxane. Examples where n and m are both non-zero include polymethyl/polymethylphenyl-siloxane, polymethylstyryl/polymethylethyl-siloxane, and polymethylstyryl/polymethyldodecyl-siloxane. In this nomenclature, the one or two substituents named after "poly" are each attached to the silicon atom in each repeating unit, and substituents before "poly" are attached to both ends of the polymer chain. To illustrate, "polymethyloctyl-siloxane" is a compound of formula (3) in which m is zero, $R_1$ is methyl, and $R_2$ is octyl. Furthermore, the term "polymethylstyryl/polymethyldodecyl-siloxane" means a compound of formula (3) wherein $R_1$ is methyl, $R_2$ is styryl (e.g. $C_6H_5CH:CH-$), $R_3$ is methyl, and $R_4$ is dodecyl (e.g. $C_{12}H_{25}-$).

The cosmetic composition can also contain 4 to 20 wt. % and preferably 6 to 15 wt. % of a cosmetically acceptable wax; those of ordinary skill in this art will readily identify what is meant by this term. Examples are carnauba, ozokerite, glyceryl tribehenate, beeswax, candelilla, paraffin, bayberry wax, lanolin, micro-crystalline wax, montan, rice wax, mono-, di- and triglyerol esters of $C_{12}$–$C_{36}$ fatty acids, polyethylene, polyethylene/polyvinyl acetate copolymers, polyethylene/polyacrylic acid copolymers, $C_{12}$–$C_{36}$ fatty alcohols, and $C_{12}$–$C_{36}$ fatty alcohol esters of $C_{12}$–$C_{36}$ fatty acids, provided that the wax is solid at room temperature (25° C.). The waxes are further characterized in that they have crystalline to microcrystalline structure; leave a film when applied to the skin from a cosmetic stick or cream; have low viscosity just above their melting points; and exhibit low solubility at room temperature in the dimethylpolysiloxane described hereinabove. Typically the waxes are high-molecular-weight hydrocarbons ($C_{12}$–$C_{100}$) or mixtures thereof, and esters of high-molecular-weight ($C_{12}$–$C_{36}$) fatty acids with high-molecular-weight ($C_{12}$–$C_{36}$) fatty alcohols, and mono-, or di- or triesters of $C_{12}$–$C_{36}$ fatty acids with glycerol.

If the cosmetic composition contain wax, it should contain enough of an organo-polysiloxane of formula (3) described above to provide that the composition, whether it is a stick, a cake, or a cream, is a single homogeneous phase. That is, above the melting point of the highest-melting ingredient one should be able to stir together a molten mixture of the three components (dimethylpolysiloxane, organo-polysiloxane, and wax) using conventional mixing equipment; and then, on discontinuing stirring, the components should not separate into discrete layers or areas of different composition. Likewise, when a stirred, molten mixture of the three components is cooled to 25° C., the cooled product should remain one continuous phase and the wax should not ooze, bleed, or otherwise separate from the siloxane and/or silane components. In general, the proper relative amounts of wax and the two silicone components can readily be determined by examination of the behavior of a sample formulation; as a general guide to formulations known to be successful, the weight percentage of the wax can be up to about one-third of the combined weight percentage of the silicone components, and the weight ratio of organo-polysiloxane (3) to dimethylpolysiloxane can be up to about 1:1. Variations from these figures are also contemplated within the broad aspect of the present invention, however, so long as the proportions chosen permit the creation of a physically stable one-phase cosmetic product. Further disclosure regarding this invention is contained in another application filed on even date herewith entitled "One-Phase Silicone-Based Cosmetic Product Containing Wax" filled by Marlene Tietjen, Jane Hollenberg, and Richard Rigg and assigned to the assignee of this application. The disclosure of that application is hereby incorporated herein by reference.

The anhydrous cosmetic composition of this invention also contains pigment which remains uniformly dispersed in the silicone better than has heretofore been known. The coated pigment is characterized by its complete hydrophobicity. That is, it is impossible to suspend or disperse even a very small amount of the coated pigment in water. The coating does not affect the color; the coated pigment exhibits the same color as the uncoated pigment. The coating is polysiloxane which is chemically bonded to the pigment; it is believed to be bonded through oxygen atoms to the surface of the pigment.

The coated pigment can exhibit structural formula (5)

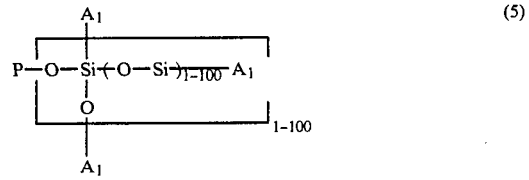

wherein each of the oxygen atoms at the left end of formula (5) is attached to an atom P in the pigment surface; and $A_1$ is an alkyl or alkenyl group having up to 30 carbon atoms. A number of adjacent polysiloxane chains as shown in (5) can be cross-linked through oxygen atoms to form a polysiloxane chain with up to 100 repeating

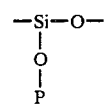

units that extends along the pigment surface, in addition to the polysiloxane chain which extends away from the pigment surface. Examples of alkyl groups are methyl, ethyl, octyl, and octadecyl. "Alkenyl" includes carbon chains with more than one double bond; examples of alkenyl groups include ethylene, propylene, acrylyl, and methacrylyl, and residues of unsaturated fatty acids such as oleic (e.g. $C_{17}H_{33}$—), linoleic ($C_{17}H_{31}$—), and linoleNic ($C_{17}H_{29}$—).

The coated pigment can also exhibit structural formula (6):

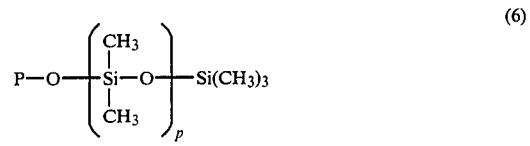

wherein p is 1-100, and P is an atom in the pigment surface.

The coated pigment can also exhibit structural formula (7):

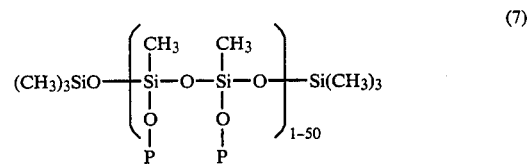

wherein P is an atom in the pigment surface, and in which each of the up to 100 repeating (Si—O) units is bonded through an oxygen atom to the pigment surface.

The number of polysiloxane chains of formulas (5), (6) and (7) that are bonded to the pigment surface is not known but is sufficiently high to coat the pigment completely and render it completely hydrophobic; hydrophobicity can readily be determined by placing the coated pigment into water and observing whether any becomes dispersed or suspended in the water.

Suitable pigments include all inorganic pigments which are usable in cosmetic formulations. Particular examples include talc, mica, titanium dioxide, iron oxide, kaolin, ultramarine, chromium oxide, chromium hydroxide, zinc oxide, silica, manganese violet, and their equivalents.

The pigment (or a mixture of two or more pigments) can be coated by placing it in dry, finely divided form in a mixer and adding a silicone material selected from the group consisting of (A) $A_1SiX_1X_2X_3$, wherein A is an alkyl or alkenyl group having 1 to 30 carbon atoms, and $X_1$, $X_2$ and $X_3$ are independently chloro, methoxy, or ethoxy (this material will form coated pigment having formula (5));

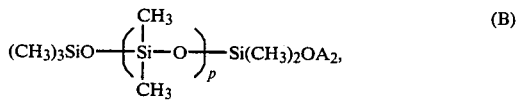
(B)

wherein p is 1 to 100 and $A_2$ is hydrogen or an alkyl group having 1 to 30 carbon atoms (this material will form coated pigment having formula (6));

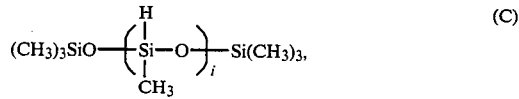
(C)

wherein i is 1 to 100 (this material will form coated pigment having formula (7)); or a one-phase mixture of two or all three of A, B, and C. The relative amounts of fluid:pigment should be sufficient to coat the pigment particles; generally a fluid:pigment weight ratio is satisfactory for which 1-4 wt. % of the final product is silicone. The pigment and fluid are intimately mixed thoroughly to obtain a uniform dispersion of the fluid on the pigment, in which the fluid completely coats the particles of pigment. The slurrying operation is advantageously carried out at a temperature of 25° C. to 160° C. effective to promote hydrolysis and reaction of the silicone with the pigment. As an alternative to synthesis, satisfactory coated pigments usable in this invention are sold in a wide variety of shades by Whittaker, Clark & Daniels, Inc., doing business as Clarks Colors; the product has the trade name Hydrophobes.

To make the cosmetic composition of the invention, one stirs the dimethylpolysiloxane component (1) with any other liquid components (such as silicone component (2), and (3) and/or (4) if liquid at room temperature) to achieve a uniform mixture. Any of the components which are initially dry (such as fillers, preservatives, and pigments, including the coated pigments described herein) are then added to the liquid mixture and dispersed using high shear equipment (such as a 3-roll mixer or Kady mill) until a homogeneous dispersion is obtained. This dispersion is then heated to a point above the melting temperature of the wax material which is to be added (usually 60°-95° C.). The wax, and any silicone component which is solid at room temperature, are added and stirred with a high-shear mixer until all components are melted and dispersed uniformly. The melted mixture is poured hot (at 60°-95° C.) into the containers of choice, e.g. pans, jars, or sticks.

The resulting product can be used per se as a cosmetic which is applied to soothe and moisturize the skin. One can also add optional ingredients such as cosmetically acceptable fillers, preservatives, and/or fragrance. Dry ingredients are added in finely divided form to the molten mixture, with stirring, before the mixture is poured into containers. Examples of fillers (added alone or in combination) are talc, mica, nylon, silica, kaolin, zinc oxide, magnesium silicate, calcium silicate, calcium carbonate, and equivalent materials, added in amounts up to about 35% by weight of the final product. Another feature of the present invention is that the filler(s) can also be silicone-coated in the same manner as the pigments described herein. Examples of preservatives are methyl and propyl parabens, and equivalents thereof, in amounts up to about 0.5 wt. %. The cosmetic formulator will recognize that any of the well-known blends of fragrance oils conventionally sold by fragrance manufacturers can be added, in amounts generally ranging up to about 0.5 wt %.

The composition can contain up to about 20 wt. % of one or more cosmetically acceptable oils, to further augment the feel of the product on the skin and to adjust the product's consistency. Suitable oils are glycerol esters and $C_3$–$C_{22}$ alcohol esters of $C_3$–$C_{22}$ fatty acids, and $C_{12}$–$C_{22}$ fatty alcohols, provided that they are liquid at 25° C. and form homogeneous mixtures with the cosmetic composition. A preferred example is 2-ethyl-1-hexyl palmitate. The ordinarily skilled formulator will recognize that other compounds known to be equivalent to those listed herein can be incorporated to the composition of this invention.

Utilization of this discovery renders the pigment easily dispersible in the formulation. The discovery also permits the preparation of products in which the pigment remains uniformly dispersed without separation. These properties are particularly advantageous at pigment contents over about 10 wt. % and even more so when the pigment content is over 40 wt. %, e.g. 40-60 wt. %. Satisfactory pigmented products with such high pigment contents were previously thought impractical or unobtainable because of the difficulty of dispersing such a high amount of pigment in the oily base. This development is particularly unexpected in view of the knowledge that pigments do not disperse well in silicone-based oils. By "pigment" we mean to include a pigment composition which is made by intimately blending amounts of two or more other unblended pigments.

Utilization of the coated pigments allows incorporation of more pigment (generally about 10-20% more) into an anhydrous cosmetic composition than is otherwise attainable. The higher pigment level provides a smooth, dry feeling makeup which has excellent slip characteristics due to the silicone fluid base.

The one-phase, anhydrous, pigmented composition preferably contains 40-60 wt. % of the coated pigment. The balance can comprise the silicone compounds (1) and (2), (3) and/or (4). Alternatively, the composition can contain optional cosmetically acceptable filler, fragrance, oil, and/or wax components. Examples of these components and typically acceptable amounts thereof are listed above.

The coated pigment and other finely divided solid particles have a size generally no larger than about 50 microns. It will be recognized that materials such as mica whose crystalline properties favor formation of flakes will be finely divided and will be up to about 150 microns in the long dimension.

The invention is further described in the following Examples.

In each Example, all components that are liquid at 25° C. were mixed together at room temperature, and then the dry ingredients (preservatives, fillers, pigments) were mixed into the liquid using high-shear equipment. When the resulting mixture was homogeneous and all solid components were uniformly dispersed, the mixture was heated to above the melting point of the wax so that was about to be added (or above the highest melting point if more than one wax was added), and then the wax was added and stirred into the mixture. If the organo-polysiloxane is a solid at 25° C., it was added at the same time as the wax. The entire mixture was stirred using conventional equipment (Lightnin brand mixer or Kady brand mill) until a uniform mixture was obtained. The mixture was poured hot (60°–95° C.) into its intended package. No phase separation or component segregation occurred during or after cooling of the product. All solid ingredients, including coated pigments, were added in finely divided form.

A foundation was prepared using this procedure except that the pigments were not coated with any silicone:

| Foundation | | |
| --- | --- | --- |
| Glyceryl tribehenate | | 6.0 |
| Polymethyloctadecylsiloxane | | 6.0 |
| 2-ethyl-1-hexyl palmitate (oil) | | 13.0 |
| Dimethylpolysiloxane (10 cs) | | 25.0 |
| Pigment | | |
| Titanium dioxide | 17.0 | |
| Iron oxide | 5.0 | |
| Talc | 15.0 | |
| Mica | 13.0 | 50.0 |

The melt viscosity of the above formulation was too high to permit it to be poured into containers. The surface of the product exhibited color striations and a mottled appearance, which indicated poor dispersion of the pigment in the product. When the pigment components were provided with a coating having formula (7) prior to incorporation into the composition, there resulted a pourable, homogeneous product. The high pigment level became an advantage rather than a drawback, and provided a smooth, dry feeling product.

Other examples, which were prepared the same way as above, in which the pigment was coated prior to addition, were:

| Cream Powder Foundation | | |
| --- | --- | --- |
| | A | B |
| Glyceryl tribehenate | 6.0 | 10.0 |
| Polymethyloctadecyl siloxane | 6.0 | — |
| 2-ethyl-1-hexyl palmitate (oil) | 13.0 | 15.0 |
| Dimethylpolysiloxane (10 cs) | 25.0 | 30.0 |
| Pigment*: | | |
| Titanium dioxide | 20.0 | 14.5 |
| Iron oxide | 7.0 | 3.0 |
| Talc | 13.0 | 9.5 |
| Mica | 10.0 | 18.0 |

*The pigment had been coated with polymethyl hydrogen siloxane.

| Eyeshadow | |
| --- | --- |
| Dimethylpolysiloxane | 10.0 |
| Glyceryl tribehenate | 6.0 |
| Candelilla | 2.0 |
| $C_{12}$–$C_{15}$ alkyl benzoate ester | 7.0 |
| Cyclomethicone D = 5 | 30.0 |
| Bismuth oxychloride | 5.0 |
| Pigment*: | 40.0 |
| Chromium oxide | 15.0 |
| Ultramarine blue | 10.0 |
| Mica | 15.0 |

*The pigment had been coated with methyl-trimethoxy silane.

What is claimed is:

1. An anhydrous homogeneous pigmented cosmetic product comprising
   (a) 10 to 70 wt. % of dimethylpolysiloxane having the formula

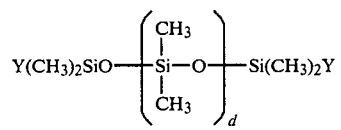

wherein both Y substituents are —$CH_3$, or both are —OH; and wherein d is sufficient to impart to the dimethylpolysiloxane a viscosity of 0.65 to $10^6$ centistokes at 25° C.; and
   (b) a coated pigment which consists essentially of finely divided particles of inorganic pigment whose surfaces are chemically bonded to, and physically completely coated by a polysiloxane which coating renders the particles hydrophobic; wherein said pigment is readily dispersible in component (a) without settling or segregating.

2. The composition of claim 1 wherein said polysiloxane coating comprises chains which have the structure

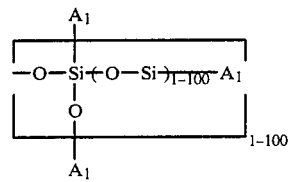

wherein $A_1$ is an alkyl or alkenyl group having up to 30 carbon atoms; or the structure

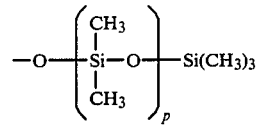

wherein p is 1–100; or the structure

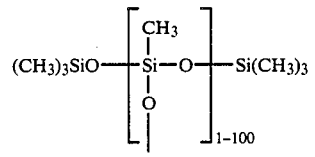

wheren there are sufficient chains bonded to each pigment particle to render the pigment hydrophobic.

3. The composition of claim 1 wherein said pigment comprises up to 60 wt. % of the composition.

4. An anhydrous homogeneous pigmented cosmetic composition comprising
(a) 10 to 70 wt. % of a silicone component comprising
  (1) dimethylpolysiloxane having the formula

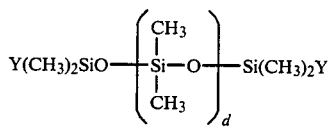

wherein both Y substituents are —CH$_3$ or both are —OH, and wherein d is sufficient to impart to the dimethylpolysiloxane a viscosity of 0.65 to 10$^6$ centistokes at 25° C.; in a one phase mixture with one or more of (2) organosilane having the formula RSi(CH$_3$)$_3$ wherein R is alkyl having 1 to 30 carbon atoms, phenyl or styryl;
  (3) organopolysiloxane having the formula

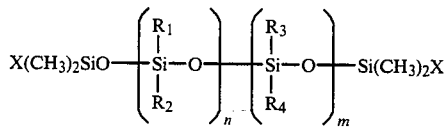

wherein
  R$_1$ and R$_3$ are independently alkyl having 1 to 30 carbon atoms, phenyl or styryl;
  X is alkyl or alkyl-oxy and has 1 to 30 carbon atoms;
  R$_4$ is alkyl having 1 to 30 carbon atoms, phenyl or styryl;
  R$_2$ is alkyl having 2 to 30 carbon atoms, phenyl or styryl, or —OSi(CH$_3$)$_3$; and
  n is 1 to 100, m is 0 to 100, and (n plus m) is 1 to 100; or
  (4) cyclomethicone having the formula

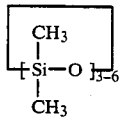

provided that said composition contains at least about 10 wt. % of component (1); and
(b) a coated pigment which comprises finely divided particles of inorganic pigment whose surfaces are chemically bonded to and physically coated by a polysiloxane which coating renders the particles hydrophobic; wherein said pigment is readily dispersible in component (a) without settling or segregating.

5. The composition of claim 4 wherein said polysiloxane coating has the structure

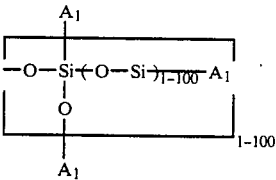

wherein A$_1$ is an alkyl or alkenyl group having up to 30 carbon atoms; or the structure

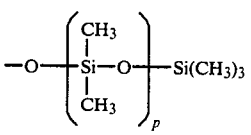

wherein p is 1–100; or the structure

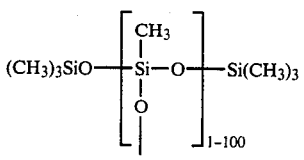

wherein there is sufficient polysiloxane bonded to each pigment particle to render the pigment hydrophobic.

6. The composition of claim 4 wherein said pigment comprises up to 60 wt. % of the composition.

7. The composition of claim 4 further comprising from 4 to 20 wt. % of a cosmetically acceptable wax, provided that there is a sufficient amount of silicone component (3) that the product formed by melting said composition and then cooling it to 25° C. is a single homogeneous phase.

8. The composition of claim 7 wherein said polysiloxane coating has the structure

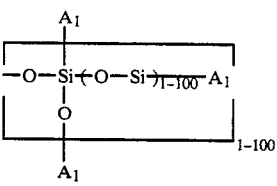

wherein A$_1$ is an alkyl or alkenyl group having up to 30 carbon atoms; or the structure

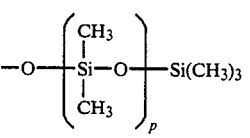

wherein p is 1–100; or the structure

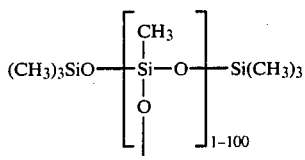

wherein there is sufficient polysiloxane bonded to each pigment particle to render the pigment hydrophobic.

9. The composition of claim 7 wherein said pigment comprises up to 60 wt. % of the composition.

10. The composition of claim 4 wherein at least one of $R_1$, $R_2$, $R_3$ and $R_4$ is alkyl.

11. The composition of claim 4 wherein said silicone component (a) comprises 20 to 50 wt. % of the composition, and said component (1) comprises at least 20 wt. % of the composition.

12. A composition according to claim 4 comprising by weight about 6 wt. % cosmetically acceptable wax, about 6% polymethyloctadecyl siloxane, about 13% of cosmetically acceptable oil, about 25% of dimethylpolysiloxane (10 cs), and about 50% polysiloxane-coated pigment.

13. A composition according to claim 4 comprising by weight about 10% cosmetically acceptable wax, about 15% cosmetically acceptable oil, about 30 wt. % dimethylpolysiloxane (10 cs), and about 45% of a polysiloxane-coated pigment.

14. A composition according to claim 4 comprising by weight about 8% cosmetically acceptable wax, about 7% cosmetically acceptable oil, about 30% cyclomethicone (D=5), about 5% pigment, about 40% polysiloxane-coated pigment, and about 10% dimethylpolysiloxane (10 cs).

* * * * *